United States Patent [19]

Hoke

[11] 3,943,114
[45] Mar. 9, 1976

[54] POLYMERS OF N-AMINOALKYL ACRYLAMIDES

[75] Inventor: Donald Irvin Hoke, Chagrin Falls, Ohio

[73] Assignee: The Lubrizol Corporation, Cleveland, Ohio

[22] Filed: Sept. 27, 1972

[21] Appl. No.: 292,564

Related U.S. Application Data

[60] Continuation-in-part of Ser. No. 203,853, Dec. 1, 1971, Pat. No. 3,883,491, which is a division of Ser. No. 832,412, June 11, 1969, Pat. No. 3,666,810.

[52] U.S. Cl. .......... 260/85.5 AM; 8/4; 162/168 NA; 210/54; 260/2.2 R; 260/80.3 N; 260/85.7; 260/86.1 N; 260/89.7 N; 260/897 R
[51] Int. Cl.$^2$ ...................... C08F 3/90; C08F 15/02
[58] Field of Search ..... 260/80.3 N, 85.7, 85.5 AM, 260/86.1 N, 89.7 N, 561 N, 561 R

[56] References Cited
UNITED STATES PATENTS

| | | | |
|---|---|---|---|
| 2,980,657 | 4/1961 | Melamed | 260/86.1 |
| 3,044,998 | 7/1962 | Emrick | 260/89.5 |
| 3,318,953 | 5/1967 | Wehrmeister | 260/558 |

Primary Examiner—Christopher A. Henderson, Jr.
Attorney, Agent, or Firm—James W. Adams, Jr.; William H. Pittman

[57] ABSTRACT

N-3-Aminoalkyl propionamides with an ether substituent on the beta carbon atom are prepared by the reaction of analogous N-3-oxohydrocarbon-substituted amides with an amine in the presence of a reducing agent, preferably hydrogen and a hydrogenation catalyst. The resulting compounds can be converted to acrylamides by pyrolysis in the presence of a strong base. The latter compounds may also be prepared by the reaction of a β,γ-unsaturated amine with an acrylonitrile in the presence of sulfuric acid. They are useful for improving dyeability of fiber-forming polymers and may be polymerized to form compositions which are useful in paper manufacture and (in their quaternized form) are excellent flocculants.

8 Claims, No Drawings

POLYMERS OF N-AMINOALKYL ACRYLAMIDES

This application is a continuation-in-part of copending application Ser. No. 203,853, filed Dec. 1, 1971 now U.S. Pat. No. 3,883,491, which is a division of application Ser. No. 832,412, filed June 11, 1969, now U.S. Pat. No. 3,666,810.

This invention relates to new compositions of matter, both monomeric and polymeric, and methods for their preparation. More particularly, it relates to compounds of the formula

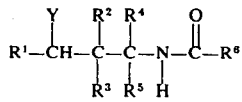

wherein each of $R^1$, $R^2$ and $R^3$ is hydrogen or a hydrocarbon radical; each of $R^4$ and $R^5$ is a hydrocarbon radical;

$R^7$ is hydrogen or a lower alkyl radical; $R^8$ is a hydrocarbon radical;

X is a salt-forming anion; $Z^1$ is hydrogen or a hydrocarbon radical and $Z^2$ is hydrogen or an alkyl or cycloalkyl radical, or

is a heterocyclic radical; and $Z^3$ is hydrogen or a lower alkyl radical.

As used herein, the term "hydrocarbon radical" includes alkyl, cycloalkyl, aryl, aralkyl and alkaryl radicals. It also includes substantially hydrocarbon radicals; that is, radicals which contain substituents such as ether, ester, nitro or halogen provided such substituents do not materially alter the character or reactivity of the radicals. The term "lower alkyl radical" denoted alkyl radicals containing no more than about 10 carbon atoms.

In the preferred embodiments of the compounds of this invention, each of $R^{1-3}$ is a hydrogen, lower alkyl, or $C_{6-15}$ aromatic radical; each of $R^4$ and $R^5$ is a lower alkyl, $C_{3-8}$ cycloalkyl or $C_{6-15}$ aromatic radical; $R^7$ is hydrogen or methyl; $R^8$ is a lower alkyl or $C_{6-15}$ aromatic radical; $Z^1$ and $Z^2$ are lower alkyl or $C_{3-5}$ cycloalkyl radicals, or

is a heterocyclic radical such as pyrrolidino, piperidino or morpholino; and X (if present) is any typical salt-forming anion such as chloride, bromide, iodide, sulfate, bisulfate, acetate, carbonate, bicarbonate or the like. More desirably, each of $R^{1-3}$ is hydrogen or lower alkyl, each of $R^4$ and $R^5$ is lower alkyl, $R^7$ is hydrogen, $R^8$ is lower alkyl, $Z^1$ and $Z^2$ are lower alkyl, and $Z^3$ (if present) is methyl.

The following are illustrative of the compounds of this invention.

N-(1,1-dimethyl-3-dimethylaminopropyl)acrylamide

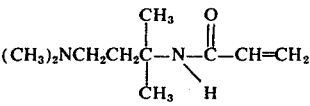

N-(1,1-dimethyl-3-dimethylaminobutyl)acrylamide

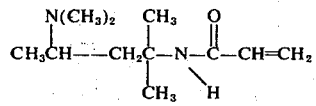

Dimethyl-3-(1-acrylamido-1,1-dimethylpropyl)ammonium chloride

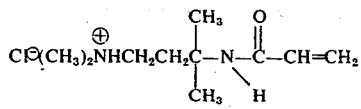

Trimethyl-3-(1-acrylamido-1,1-dimethylbutyl)ammonium iodide

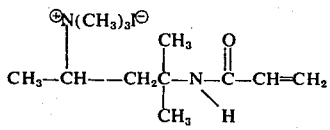

N-(1-methyl-1,3-diphenyl-3-diethylaminopropyl)methacrylamide

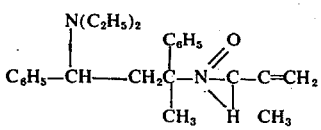

N-[1-methyl-1,3-(p-chlorophenyl)-3-pyrrolidinopropyl]acrylamide

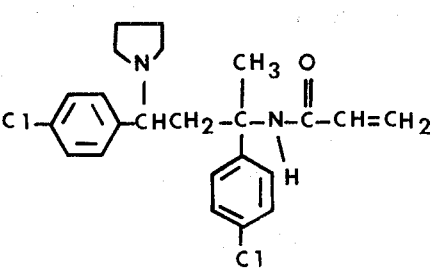

N-(1,1-dimethyl-3-dimethylaminobutyl)-3-methoxypropionamide

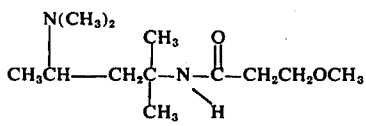

N-(1,1-dimethyl-3-methylanilinobutyl)-3-ethoxy-proprionamide

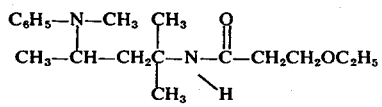

N-(1,1-dimethyl-3-piperidinopropyl)-3-phenoxy-2-methylpropionamide

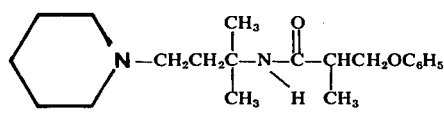

Trimethyl-3-[1-(3-methoxypropionamido)-1-methyl-1,3-diphenylpropyl]ammonium iodide

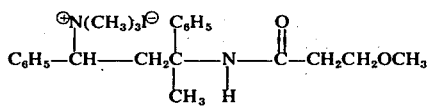

N-[1-(2-dimethylaminocyclohexyl)-1-cyclohexyl]-3-(p-nitrophenyl)propionamide

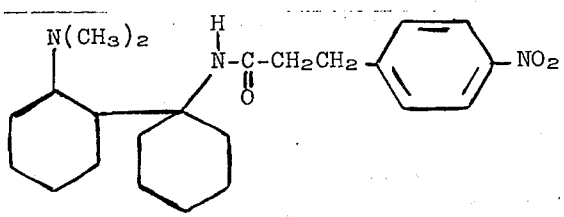

Compounds of the present invention wherein

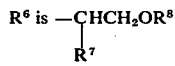

(hereinafter sometimes referred to as "oxy compounds") may be prepared by reacting an oxyproprionamide of the formula

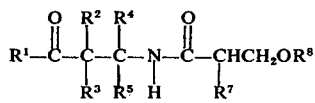

with an amine of the formula

in the presence of a reducing agent. Oxypropionamides of the above formula may be obtained by the reaction of a hydroxy compound (alcohol or phenol, preferably an alcohol) with an N-3-oxohydrocarbon-substituted acrylamide of the type disclosed in U.S. Pat. Nos. 3,277,056 and 3,425,942. The reaction leading to the oxypropionamide is disclosed in U.S. Pat. No. 3,647,875. The disclosures of these patents are hereby incorporated by reference in the present specification.

The reaction of the oxypropionamide with the amine is of the type generally identified as "reductive amination". A typical example of such a reaction is the Leuckart reaction, in which an oxo compound is reacted with an amine in the presence of formic acid, or with an amine formate, with the result that the carbon atom formerly part of the oxo group is aminated and carbon dioxide and water are evolved as by-products.

A preferred method for reductive amination of the oxypropionamide involves its reaction with the amine in the presence of hydrogen and a hydrogenation catalyst such as platinum/platinum oxide, palladium, copper chromite or Raney nickel. Of these catalysts, platinum/platinum oxide (Adams' catalyst) is preferred. (It is referred to as "platinum/platinum oxide" because it is usually introduced as the oxide, but is immediately reduced to elemental platinum upon contact with hydrogen.) Typically, the oxypropionamide and the amine are mixed and a small amount of the hydrogenation catalyst is added; the mixture is then pressurized with hydrogen to at least about 50 psi. and agitated, typically at a temperature of about 25°–100°C. and usually with periodic replenishment of the hydrogen pressure, until hydrogen uptake has ceased. The reductive amination may be effected in the presence of a suitable solvent such as an alcohol, ether or the like, but such solvent is frequently unnecessary. It has also been found that the presence of a small amount (usually about 0.1–5.0% by weight of the reaction mixture) of an acid increases the reaction rate. Typical acids which may be used are aromatic sulfonic acids, mineral acids, perchloric acid and amine salts thereof, and the like.

The molar ratio of amine to oxypropionamide in the reaction mixture should be at least 1:1, and is generally greater (up to about 5:1). Ratios between about 1.25:1 and 3:1 are preferred.

Following completion of the reductive amination reaction, the product may be isolated and purified in the customary ways.

The following examples illustrate the preparation of oxy compounds of the present invention. All parts, percentages and proportions are by weight unless otherwise stated.

EXAMPLE 1

To a mixture of 201 parts (1 mole) of N-(1,1-dimethyl-3-oxobutyl)-3-methoxypropionamide and 91 parts (2 moles) of dimethylamine are added 0.5 part of platinum oxide and 3 parts of p-toluenesulfonic acid. The liquid mixture is poured into a hydrogenation bottle, flushed with hydrogen and pressurized with hydrogen on a Parr hydrogenation apparatus at 69 psi. and hydrogenated for about 12 hours, with hydrogen pressure being replenished to 70 psi. when it has dropped to 27 psi. The mixture is then stripped on a rotary evaporator and the residue, a yellow liquid, is dissolved in 16% aqueous hydrochloric acid and extracted with four 100-ml. portions of chloroform. The aqueous solution is then made alkaline by the addition of a solution of 30 parts of sodium hydroxide in 75 parts of water, the alkaline solution is again extracted with four 100-ml. portions of chloroform and the chloroform extracts are stripped and distilled. The desired product, N-(1,1-dimethyl-3-dimethylaminobutyl)-3-methoxypropionamide, is obtained boiling at 87°–95°C./0.5 mm. It contains 12.1% nitrogen, as compared with 12.2% theoretical.

EXAMPLE 2

Following the procedure of Example 1, 263 parts (1 mole) of N-(1,1-dimethyl-3-oxobutyl)-3-phenoxypropionamide is reacted with 95 parts (2.11 moles) of dimethylamine in the presence of 1.75 parts of 70% aqueous perchloric acid and 0.5 part of platinum oxide. The product is N-(1,1-dimethyl-3-dimethylaminobutyl)-3-phenoxypropionamide.

EXAMPLE 3

The procedure of Example 2 is repeated, except that the phenoxypropionamide used therein is replaced by 216 parts (1 mole) of N-(1,1-dimethyl-3-oxobutyl)-3-methoxy-1-methylpropionamide. The product is N-(1,1-dimethyl-3-dimethylaminobutyl)-3-methoxy-1-methylpropionamide.

EXAMPLE 4

A one-gallon autoclave, fitted with a stirrer, is charged with 1684 parts (8.38 moles) of N-(1,1-dimethyl-3-oxobutyl)-3-methoxypropionamide, 762 parts (16.9 moles) of dimethylamine, 1.5 parts of platinum oxide and 15 parts of dimethylammonium perchlorate. The autoclave is pressurized with hydrogen to 750 psi., and stirring is begun. Hydrogen pressure is periodically restored to 850–900 psi. and stirring is continued until hydrogen uptake has ceased. Sodium bicarbonate, 10 parts, is added to the mixture which is then stripped, acidified, extracted with chloroform, made alkaline and again extracted with chloroform as in Example 1. The chloroform extract from the alkaline solution is stripped and distilled, and the product, N-(1,1-dimethyl-3-dimethylaminobutyl)-3-methoxypropionamide, is obtained boiling at 108°C./0.9 mm. The yield is 1418.6 parts, or 73.6% of the theoretical amount.

EXAMPLE 5

The procedure of Example 4 is repeated, except that the methoxypropionamide used therein is replaced by 325 parts (1 mole) of N-(1,3-diphenyl-1-methyl-3-oxopropyl)-3-methoxypropionamide. The product is N-(1,3-diphenyl-1-methyl-3-dimethylaminobutyl)-3-methoxypropionamide.

EXAMPLE 6

To a solution of 20.1 grams (0.1 mole) of N-(1,1-dimethyl-3-oxobutyl)-3-methoxypropionamide and 10 grams (0.137 mole) of diethylamine in 100 ml. of methanol is added 0.25 gram of Raney nickel. The mixture is placed in a hydrogenation bottle and charged with hydrogen to 260 psi. It is then placed on a Parr hydrogenation apparatus and hydrogenated at 50°C. until hydrogen uptake is complete. The product, isolated as described in Example 1, is N-(1,1-dimethyl-3-diethylaminobutyl)-3-methoxypropionamide.

EXAMPLE 7

Following the procedure of Example 4, a mixture of 201 parts (1 mole) of N-(1,1-dimethyl-3-oxobutyl)-3-methoxypropionamide, 170 parts (2 moles) of piperidine, 0.5 part of platinum oxide and 1 part of dimethylammonium perchlorate is hydrogenated in the Parr apparatus, starting at a pressure of 70 psi. and recharging when the pressure has reached 39 psi. After workup as described in Example 4, the desired product, N-(1,1-dimethyl-3-piperidinobutyl)-3-methoxypropionamide, is obtained boiling at 112°–115°C./0.25 mm.

EXAMPLE 8

Following the procedure of Example 1, 20.1 grams (0.1 mole) of N-(1,1-dimethyl-3-oxobutyl)-3-methoxypropionamide is reacted with 10 grams (0.14 mole) of pyrrolidine in the presence of 0.3 gram of platinum oxide and 100 ml. of methanol. When hydrogen uptake has ceased, the methanol is stripped and the product, N-(1,1-dimethyl-3-pyrrolidylbutyl)-3-methoxypropionamide, is isolated as described in Example 1.

EXAMPLE 9

Following the procedure of Example 1, N-(1,1-dimethyl-3-morpholinobutyl)-3-methoxypropionamide is prepared by the reaction of 201 parts (1 mole) of N-(1,1-dimethyl-3-oxobutyl)-3-methoxypropionamide with 174 parts (2 moles) of morpholine in the presence of 0.5 part of platinum oxide and 1 part of dimethylammonium perchlorate.

EXAMPLE 10

The procedure of Example 4 is repeated, except that the dimethylamine is replaced by 1810 parts (16.9 moles) of methylaniline. The product is N-(1,1-dimethyl-3-methylanilinobutyl)-3-methoxypropionamide.

The compounds of this invention wherein

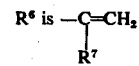

(hereinafter sometimes referred to as "acrylamido compounds") may be obtained from the oxy compounds described above by elimination of $R^8OH$ by any of several methods which are known per se. Typical methods are described briefly in a recent review: P. F. Butskus et al., *Russian Chemical Reviews*, 35, 39 (1966). The preferred method is pyrolysis in the presence of a basic reagent, ordinarily a strong base such as solid sodium hydroxide, at about 70°–150°C. This reaction is conveniently carried out at reduced pressure.

Another method for preparation of acrylamido compounds of this invention is by the reaction of a nitrile of the formula

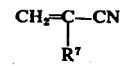

with a β, γ-unsaturated amine of the formula

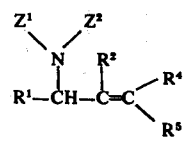

in the presence of sulfuric acid. Unsaturated amines of this type may be prepared by the reaction of a compound of the formula

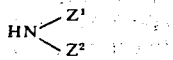

with a 1,3-diene, usually in the presence of a strongly alkaline catalyst such as metallic sodium. This is a typical 1,4-addition reaction, known in the art.

For the reaction of the unsaturated amine with the nitrile, it is usually preferred to use at least about 1.5 moles, typically about 1.9–3.0 moles, of the nitrile per mole of unsaturated amine. The sulfuric acid should be at least about 90%, and preferably 96–98%, in strength and the molar ratio of sulfuric acid to amine should be at least about 1:1, and preferably between about 1.1:1 and 2:1. Solvents are usually unnecessary, but it may be advantageous to add a small amount of a polymerization inhibitor such as hydroquinone, a hindered phenol or the like. When the reaction is complete, the product may be isolated by diluting and neutralizing the mixture and separating the unsaturated amide by traditional techniques.

The preparation of acrylamido compounds of this invention is illustrated by the following examples.

EXAMPLE 11

A mixture of 144.7 parts (0.63 mole) of N-(1,1-dimethyl-3-dimethylaminobutyl)-3-methoxypropionamide, 1 part of solid sodium hydroxide and 1 part of hydroquinone is charged to a reaction flask fitted with a condenser with a Dry Ice-cooled receiver, a stirrer and temperature control means. The pressure in the flask is reduced to less than 5 mm. and the flask is heated to 80°C. Vigorous reaction begins and liquid condenses in the receiver. After about one-half hour, the temperature is increased to 90°C. and this temperature is maintained for 3 hours. The product is distilled and the desired N-(1,1-dimethyl-3-dimethylaminobutyl)acrylamide is obtained at 80°–91°C./0-.3–0.4 mm. The yield is 109.1 parts, or 87.4% of the theoretical amount, and the nitrogen percentage is the calculated 14.1%.

EXAMPLES 12–14

The procedure of Example 11 is repeated starting with, respectively, N-(1,3-diphenyl-1-methyl-3-dimethylaminopropyl)-3-methoxypropionamide, N-(1,1-dimethyl-3-piperidinobutyl)-3-methoxypropionamide, and N-(1,1-dimethyl-3-methylanilinobutyl)-3-methoxypropionamide. The corresponding acrylamides are obtained.

EXAMPLE 15

To a mixture of 273 parts (4 moles) of isoprene and 2 parts (0.087 mole) of sodium metal, at 0°C., is added 180 parts (4 moles) of dimethylamine over one hour. The temperature is maintained below 12°C. by cooling with a Dry Ice-isopropanol-filled cooling coil. After the dimethylamine addition is complete, the mixture is stirred and cooled for an additional 3½ hours. Methanol, 6 parts, is then added to decompose the sodium and the mixture is distilled. The fraction boiling at 117.5°–119.5°C. is the desired 1-dimethylamino-3-methyl-2-butene.

A resin flask is cooled to 0°C. and 450 grams (8.5 moles) of acrylonitrile, 1020 grams (10 moles) of sulfuric acid and 37 grams of water are added. To this mixture are then added 475 grams (4.2 moles) of the 1-dimethylamino-3-methyl-2-butene prepared as described above, and 8.5 grams of 2,6-di-t-butyl-p-cresol. The mixture is stirred at 68°C. for about 1 hour and is then neutralized with about 30% sodium hydroxide. The organic layer is separated, diluted with 2050 ml. of methanol and neutralized with ammonia. An additional 1000 ml. of methanol is added and the solution is filtered. The methanol is stripped from the filtrate and the residue is distilled. There is obtained 400 grams (64.5% of the theoretical amount) of the desired N-(1,1-dimethyl-3-dimethylaminopropyl)acrylamide boiling at 75°–92°C./0.25–0.9 mm. The nitrogen analysis is 15.4%, as compared with a theoretical value of 15.2%.

The amino compounds prepared as described above may be converted into amine salts by reaction with a suitable acid, or into quaternary ammonium salts by reaction with an alkyl halide, sulfate or the like. This is illustrated in the following examples.

EXAMPLE 16

Methyl iodide, 2.8 grams (0.0197 mole), is added to a solution of 3.6 grams (0.0182 mole) of N-(1,1-dimethyl-3-dimethylaminobutyl)acrylamide in 10 ml. of benzene. An exothermic reaction takes place and the temperature of the mixture is held at 25°–30°C. by external cooling. Upon stirring overnight, a gummy solid precipitates; this solid is separated and recrystallized from a mixture of methanol and benzene. There is obtained 4.7 grams of the desired trimethyl-3-(1-acrylamido-1,1-dimethylbutyl)ammonium iodide.

EXAMPLE 17

Hydrogen chloride is bubbled through a solution of 5 grams of N-(1,1-dimethyl-3-dimethylaminopropyl)acrylamide in benzene. The desired dimethyl-3-(1-acrylamido-1,1-dimethylpropyl)ammonium chloride precipitates and is separated by filtration.

The oxy compounds of this invention are useful primarily as chemical intermediates for the preparation of acrylamido compounds, as described hereinabove.

The acrylamido compounds of this invention are readily polymerized, either alone or with other monomers. The term "polymer", as used herein, includes homopolymers, copolymers, terpolymers and other interpolymers.

The free-radical method is generally the most convenient one for polymerization of the compounds of this invention. Polymerization by this method may be effected in bulk, solution, suspension or emulsion, by contacting the monomer or monomers with a polymerization initiator either in the absence or presence of a diluent at a temperature of about 0°–200°C. Suitable free-radical initiators include benzoyl peroxide, tertiary butyl hydroperoxide, acetyl peroxide, hydrogen peroxide, azobisisobutyronitrile, sodium persulfate, ammonium persulfate-sodium metabisulfite, chlorate-sulfite and the like. Solution polymerization may be effected in an organic solvent such as benzene, toluene, cyclohexane, n-hexane, naphtha, tetrahydrofuran, mineral oil or the like; emulsion and suspension polymerization are conveniently effected in water or a mixture of water with a hydroxylated organic solvent.

Free-radical polymerization of the monomers of this invention may also be effected by photoinitiation techniques using ultraviolet, visible or infrared radiation. For these methods, the presence of suitable initiators and sensitizers, which are known in the art, is required.

Suitable emulsifiers for use in the preparation of emulsion polymers of this invention include cationic materials such as stearyl dimethyl benzyl ammonium chloride; non-ionic materials such as alkyl aryl polyether alcohols and sorbitan mono-oleate; anionic materials such as sodium decylbenzene sulfonate, dioctyl sodium sulfosuccinate, sodium salts of alkyl aryl polyether sulfates, and sodium lauryl sulfate; alkali metal salts of lignosulfonic acids, silicic acids and the like; and colloidal materials such as casein, sodium polyacrylate, carboxymethylcellulose, hydroxyethylcellulose, gum tragacanth, sodium alginate, gelatin, methylcellulose, gum arabic, dextrins or polyvinyl alcohol.

A large variety of monomers can be used to form interpolymers with the compounds of this invention. For the most part, these monomers are polymerizable vinyl compounds. They include (1) esters of unsaturated alcohols, (2) esters of unsaturated acids, (3) esters of unsaturated polyhydric alcohols (e.g., butenediol), (4) vinyl cyclic compounds, (5) unsaturated ethers, (6) unsaturated ketones, (7) unsaturated amides, (8) unsaturated aliphatic hydrocarbons, (9) vinyl halides, (10) unsaturated acids, (11) unsaturated acid anhydrides, (12) unsaturated acid chlorides, and (13) unsaturated nitriles. Specific illustrations of such compounds are:

1. Esters of unsaturated alcohols: Allyl, methallyl, crotyl, 1-chloroallyl, 2-chloroallyl, cinnamyl, vinyl, methylvinyl, 1-phenallyl, butenyl esters of (a) saturated acids such as acetic, propionic, butyric, valeric, caproic and stearic; (b) unsaturated acids such as acrylic, alpha-substituted acrylic (including alkylacrylic, e.g., methacrylic, ethylacrylic, propylacrylic, etc., and arylacrylic such as phenylacrylic) crotonic, oleic, linoleic and linolenic; (c) polybasic acids such as oxalic, malonic, succinic, glutaric, adipic, pimelic, suberic, azelaic and sebacic; (d) unsaturated polybasic acids such as maleic, fumaric, citraconic, mesaconic, itaconic, methylenemalonic, acetylenedicarboxylic and aconitic; (e) aromatic acids, e.g., benzoic, phenylacetic, phthalic, terephthalic and benzoylphthalic acids.

2. Esters of saturated alcohols, such as methyl, ethyl, propyl, isopropyl, butyl, isobutyl, sec-butyl, tert-butyl, 2-ethylhexyl, cyclohexyl or behenyl alcohols, with unsaturated aliphatic monobasic and polybasic acids, examples of which are illustrated above.

3. Esters of unsaturated polyhydric alcohols, e.g., butenediol, with saturated and unsaturated aliphatic and aromatic, monobasic and polybasic acids, illustrative examples of which appear above.

4. Vinyl cyclic compounds including (a) monovinyl aromatic hydrocarbons, e.g., allylbenzene, styrene, o-, m-, p-chlorostyrenes, -bromostyrenes, -fluorostyrenes, -methylstyrenes, -ethylstyrenes, -cyanostyrenes; di-, tri-, and tetra-, etc., -chlorostyrenes, -bromostyrenes, -fluorostyrenes, -methylstyrenes, -ethylstyrenes, -cyanostyrenes; vinylnaphthalene, vinylcyclohexane; (b) corresponding polyvinyl compounds such as divinylbenzene and trivinylbenzene; and (c) vinyl heterocycles such as vinylfuran, vinylpyridine, vinylbenzofuran, N-vinylcarbazole, N-vinylpyrrolidone, N-vinylthiopyrrolidone and N-vinyloxazolidone.

5. Unsaturated ethers such as methyl vinyl ether, ethyl vinyl ether, cyclohexyl vinyl ether, octyl vinyl ether, diallyl ether, ethyl methallyl ether and allyl ethyl ether.

6. Unsaturated ketones, e.g., methyl vinyl ketone and ethyl vinyl ketone.

7. Unsaturated amides, such as acrylamide, methacrylamide, N-methylacrylamide, N-phenylacrylamide, N-allylacrylamide, N-methylolacrylamide, N-allylcaprolactam, diacetone acrylamide and N-(1,1-dimethyl-3-hydroxybutyl)acrylamide.

8. Unsaturated aliphatic hydrocarbons, for instance, ethylene, propylene, butenes, butadiene, isoprene, 2-chlorobutadiene and alpha-olefins in general.

9. Vinyl halides, e.g., vinyl fluoride, vinyl chloride, vinyl bromide, vinylidene chloride, vinylidene bromide, allyl chloride and allyl bromide.

10. Unsaturated acids (for example, acrylic, methacrylic, propylacrylic), examples of which appear above.

11. Unsaturated acid anhydrides, e.g., maleic, citraconic, itaconic, cis-4-cyclohexene-1,2-dicarboxylic and bicyclo(2,2,1)-5-heptene-2,3-dicarboxylic anhydrides.

12. Unsaturated acid halides such as cinnamoyl, acrylyl, methacrylyl, crotonyl, oleyl and fumaryl chlorides or bromides.

13. Unsaturated nitriles, e.g., acrylonitrile, methacrylonitrile and other substituted acrylonitriles.

The preferred comonomers are vinyl esters of carboxylic acids, illustrated by vinyl acetate; alkyl esters of unsaturated carboxylic acids, illustrated by ethyl acrylate, 2-ethylhexyl acrylate and methyl methacrylate; unsaturated nitriles such as acrylonitrile; and unsaturated amides such as acrylamide, N-methylacrylamide and methacrylamide.

The relative proportions of the compounds of this invention and the comonomers to be used in interpolymerization depend upon the reactivity of these monomers as well as the properties desired for the interpolymers being formed. To illustrate, interpolymers in which rigidity is desired are obtained by polymerization of a mixture of monomers having a few substitutions or substitutions of relatively short chain length. If a still higher degree of rigidity is desired, a monomer mixture may be used in which a small amount of a bifunctional monomer is included such as divinylbenzene which will crosslink the polymer.

The polymers of this invention can also be prepared from polymers of N-3-oxohydrocarbon-substituted acrylamides such as N-(1,1-dimethyl-3-oxobutyl)acrylamide (diacetone acrylamide) by reductive amination, using techniques and conditions similar to those described herein for the preparation of oxy compounds of this invention.

Polymers of this invention wherein Y is an amino group can be converted to salts, including quaternary ammonium salts, by the same methods described herein for monomers; or polymeric salts may be obtained from monomeric salts by ordinary polymerization means.

The preparation of polymers of this invention is illustrated by the following examples.

EXAMPLE 18

A solution of 10 parts of N-(1,1-dimethyl-3-dimethylaminobutyl)acrylamide in 40 parts of benzene is flushed with nitrogen for 10 minutes, and 0.05 part of benzoyl peroxide is added. The solution is heated at 60°–65°C. for 16 hours, after which an additional 0.05 part of benzoyl peroxide is added. Heating is continued for 16 hours, after which the benzene is removed by evaporation, leaving a viscous oil. This oil is dissolved in methanol and the solution is poured into water. The desired homopolymer of N-(1,1-dimethyl-3-dimethylaminobutyl)-acrylamide precipitates and is air dried.

EXAMPLE 19

Four grams (0.202 mole, based on monomer) of the polymer of Example 18 is dissolved in 25 ml. of methanol and 2.85 grams (0.202 mole) of methyl iodide is added. The solution is heated at 50°–60°C. for 1½ hours, during which time a white precipitate forms. The liquid is removed by decantation and the precipitate, which is the desired poly-[trimethyl-3-(1-acrylamido-1,1-dimethylbutyl)ammonium iodide], is washed with acetone and air dried.

EXAMPLE 20

A mixture of 20 parts of N-(1,1-dimethyl-3-dimethylaminobutyl)acrylamide, 80 parts of water and 0.1 part of sodium lauryl sulfate is purged with nitrogen for one-half hour, and then a solution of 0.1 part of ammonium persulfate in one part of water is added. The solution is stirred as polymerization takes place. The mixture is allowed to stand overnight and is then filtered. The desired suspension homopolymer is air dried.

EXAMPLE 21

A solution of 20 parts (0.109 mole) of N-(1,1-dimethyl-3-dimethylaminopropyl)acrylamide in 8.5 parts of water is purged with nitrogen and 0.5 part of ammonium persulfate is added. The mixture is stirred for about 1½ hours, during which time polymerization takes place. Water, 175 parts, is then added followed by 13.7 parts (0.109 mole) of dimethyl sulfate. An exothermic reaction takes place as stirring is continued overnight. There is obtained an aqueous solution of the quaternized homopolymer from which water is removed by evaporation and vacuum drying.

EXAMPLE 22

The procedure of Example 18 is repeated, except that the monomer is replaced on an equal weight basis with N-(1,3-diphenyl-1-methyl-3-dimethylaminopropyl)acrylamide. A similar homopolymer is obtained.

EXAMPLE 23

The procedure of Example 18 is repeated, except that the monomer is replaced on an equal weight basis by N-(1,1-dimethyl-3-methylanilinobutyl)acrylamide. A similar homopolymer is obtained.

EXAMPLE 24

To a solution of one part of N-(1,1-dimethyl-3-dimethylaminobutyl)acrylamide in 5 parts of water is added 0.1 part of methylene blue and a solution of 0.2 part of triethanolamine in 10 parts of water. The solution is exposed to an infrared heat lamp, and polymerization begins after about 3 seconds as evidenced by the dissipation of blue color in the solution and the formation of a hazy precipitate.

EXAMPLES 25–27

Copolymers of acrylonitrile with N-(1,1-dimethyl-3-dimethylaminobutyl)acrylamide are prepared, respectively, from 49.5 parts of acrylonitrile and 0.5 parts of the acrylamide, 47.5 parts of acrylonitrile and 2.5 parts of the acrylamide, and 45 parts of acrylonitrile and 5 parts of the acrylamide. In each case, the polymerization is effected by dissolving the monomers in 600 parts of water, flushing with nitrogen and adding a solution of 0.25 part of ammonium persulfate in 1 part of water. When precipitation of the copolymer is complete, it is removed by filtration, washed with water and dried in a vacuum oven.

EXAMPLE 28

Dimethyl sulfate, 2.03 parts, is added to a solution of 2.97 parts of N-(1,1-dimethyl-3-dimethylaminopropyl)acrylamide in 225 parts of water, with stirring. An exothermic reaction takes place over about one-half hour. Acrylamide, 15 parts, is then added and the solution is purged with nitrogen, after which time about 0.5 gram of ammonium persulfate is added. Polymerization takes place over 4 hours, and after this time 200 parts of water is added and stirring is continued. A homogenous mixture is obtained which is diluted with water to a 1% solution of the desired quaternized copolymer.

EXAMPLE 29

A mixture of 40 parts of vinyl acetate, 10 parts of N-(1,1-dimethyl-3-dimethylaminobutyl)acrylamide, 0.5 part of sodium lauryl sulfate and 450 parts of distilled water is flushed with nitrogen, and a solution of 0.25 part of ammonium persulfate in 1 part of water is added. The mixture is heated to 55°C., with stirring, and is held at this temperature for one hour. The product is an emulsion of the desired copolymer.

EXAMPLE 30

Following the procedure of Examples 25–27, a copolymer is prepared from 30 parts of ethyl acrylate, 20 parts of N-(1,1-dimethyl-3-dimethylaminobutyl)acrylamide, 450 parts of water, 0.5 part of sodium lauryl sulfate and a solution of 0.25 part of ammonium persulfate in 1 part of water. The polymer which is obtained by coagulation is filtered and dried in a vacuum oven.

The acrylamido compounds of this invention, when copolymerized with acrylonitrile or methacrylonitrile, provide reactive sites in the copolymer which result in improved dyeability as compared with acrylonitrile polymers not containing such sites. This improved dyeability is shown, in general, by polymers containing about 0.5–20.0% by weight of units derived from the compounds of this invention.

The effectiveness of the polymers of this invention as dyeability improvers for polyacrylonitrile is shown by a test in which films of the copolymers of Examples 25–27 are suspended for 1½ hours in a 0.05% aqueous solution of Orange II dye at 80°–98°C., washed with distilled water and dried. The degree of coloration of the films increases in proportion to the percentage of units derived from N-(1,1-dimethyl-3-dimethylaminobutyl)acrylamide in the polymers. A film of an acrylonitrile homopolymer, treated similarly, is uncolored.

Polymers of the acrylamido compounds of this invention may be blended with olefin polymers, especially polyethylene and polypropylene, to improve the dyeability thereof. The resulting blends contain a minor amount, usually about 1–20% by weight, of the polymer of this invention. The effectiveness of such polymers as dyeability improvers for polypropylene is shown by a test in which 2.5 parts, 5.0 parts and 7.5 parts, respectively, of a homopolymer similar to that of Example 20 are blended with 50 parts of polypropylene. Sufficient methanol is added to cover the polypropylene and the mixtures are shaken for one minute and allowed to stand in closed bottles for 40 minutes. The bottles are then opened and methanol is removed by evaporation at room temperature and finally in a vacuum oven at 48°–50°C. Films of the resulting modified polypropylene samples are suspended in the Orange II dye solution described above at 60°–90°C. for 2¼ hours. The strips are then removed, rinsed with distilled water and dried. Each of the strips is noticeably colored by the dye.

Polymers of the acrylamido compounds of this invention are useful in the manufacture and treatment of paper. The polymers containing free amine groups are primarily useful as dry and wet strength improvers; for this use, a solution of polymer in water, a polar solvent such as a lower alkanol, or a combination of water and said polar solvent is ordinarily added to the aqueous slurry of fibers which is used to make the paper. These fibers are usually cellulosic materials such as hemp, cotton, wood pulp or reclaimed waste paper. According to well known procedures, the aqueous slurry is then ordinarily deposited on a continuously moving mesh or perforated surface such as a hollow cylinder or Fourdrinier wire, and the water is removed from said slurry. Typically, drainage and suction are used to decrease the water content of the slurry to about 80%, after which rolls and presses assisted by evaporation are used to remove the remaining water and form a dry sheet. The amount of the polymer of this invention which is generally used is about 1.5–20.0%, based on the weight of the dry paper.

It is also possible to saturate the formed paper sheet with a solution of the polymer of this invention and subsequently evaporate the solvent to produce a paper having improved dry and wet strength. The relative amount of polymer used is the same in this method as in the method described immediately hereinabove.

The polymers of this invention containing quaternary ammonium salt groups are also useful to improve dry and wet strength of paper; they may also be used to retention aids and flocculants when incorporated in the aqueous slurry of fibers as described hereinabove.

The utility of the polymers of this invention as dry strength improvers is shown by a test in which strips of filter paper are saturated with a 5% solution in methanol of the polymer of Example 20 and dried by suspension for 2 hours at room temperature. The average tensile strength of the treated strips, as measured on a Instron tester using a crosshead speed of 0.2 inch per minute at a temperature of 72°F., was 21.6 pounds per inch width, as compared with 13.8 pounds for untreated specimens.

Quaternized polymers of this invention are useful for flocculating solids suspended in an aqueous medium. This utility finds practical application in paper manufacture, as described above, and also in the treatment of sewage-containing effluents and in industrial processes for the deposition and recovery of various kinds of suspended solids from water.

Flocculation is accomplished by merely adding an effective amount of the quaternized polymer to the suspension being treated. The amount added is usually between 0.01 and 20 ppm.

The effectiveness of the quaternized polymers of this invention as flocculants for the precipitation of kaolin is shown by a test in which one part of kaolin is suspended in 100 parts of water and about 0.01 part of a 20% aqueous solution of the homopolymer of Example 19 is added. The suspension is shaken for about one-half minute and allowed to stand. A flocculent precipitate forms immediately. By contrast, the kaolin in a control sample which is not treated with the homopolymer of Example 19 remains suspended.

The effectiveness of the polymers as flocculants for raw sewage is shown by a test in which 600 ml. of sewage is placed in a beaker and an aqueous solution of the quaternized polymer is added, with rapid stirring. The rapid stirring is continued for 3 minutes, followed by 12 minutes of slow stirring and 15 minutes of settling. A 50-ml. aliquot is then removed from the top half inch of the mixture and its turbidity is measured on a Bryce-Phoenix light scattering photometer. The results are shown in the following table.

| Flocculant | Concentration, ppm. | Turbidity |
|---|---|---|
| Homopolymer of Ex. 21 | 1 | 2.57 |
|  | 2 | 2.03 |
|  | 4 | 0.931 |
|  | 8 | 0.400 |
|  | 10 | 0.152 |
|  | 12 | 0.112 |
|  | 13 | 0.090 |
| Copolymer of Ex. 28 | 1 | 1.39 |
|  | 2 | 0.570 |
|  | 4 | 0.306 |
|  | 8 | 0.136 |
|  | 10 | 0.067 |

The monomers of this invention, by virtue of their susceptibility to photoinitiated polymerization, are useful in photoengraving and photographic techniques. They may also be copolymerized with crosslinking agents such as divinylbenzene, in the presence of suspending agents such as bentonite, to form cationic ion exchange resins.

What is claimed is:

1. A polymer of a compound of the formula

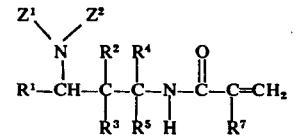

wherein each of $R^1$, $R^2$ and $R^3$ is hydrogen or a hydrocarbon radical; each of $R^4$ and $R^5$ is a hydrocarbon radical; $R^7$ is hydrogen or a lower alkyl radical; and each of $Z^1$ and $Z^2$ is a lower alkyl or $C_{3-8}$ cycloalkyl radical, or

is a heterocyclic radical.

2. A polymer according to claim 1 wherein $R^7$ is hydrogen or methyl.

3. A compound according to claim 2 wherein each of $R^1$, $R^2$ and $R^3$ is hydrogen or a lower alkyl radical, each of $R^4$ and $R^5$ is a lower alkyl radical, $R^7$ is hydrogen, and each of $Z^1$ and $Z^2$ is a lower alkyl radical.

4. A polymer according to claim 3 which is a homopolymer.

5. A polymer according to claim 3 which is an interpolymer of said compound with at least one polymerizable vinyl monomer.

6. An interpolymer according to claim 5 wherein the polymerizable vinyl monomer is a vinyl ester of a carboxylic acid, an alkyl ester of an unsaturated carboxylic acid, an unsaturated nitrile, or an unsaturated amide.

7. An interpolymer according to claim 6 which is a copolymer of said compound with acrylonitrile or methacrylonitrile.

8. A copolymer according to claim 7 wherein $R^1$ is hydrogen or methyl; $R^2$, $R^3$ and $R^7$ are hydrogen; $R^4$ and $R^5$ are methyl; and each of $Z^1$ and $Z^2$ is methyl.

* * * * *